(12) United States Patent
Matsumoto et al.

(10) Patent No.: US 8,293,190 B2
(45) Date of Patent: *Oct. 23, 2012

(54) POLYMER COMPOUND FOR BIOMEDICAL USE AND BIOCHIP SUBSTRATE USING SUCH A POLYMER COMPOUND

(75) Inventors: Mitsutaka Matsumoto, Tokyo (JP); Sumio Shibahara, Tokyo (JP); Takayuki Matsumoto, Tokyo (JP); Kanehisa Yokoyama, Tokyo (JP); Sohei Funaoka, Tokyo (JP); Daisuke Masuda, Tokyo (JP); Michael Patrick Coleman, Louisville, CO (US); Dominic Zichi, Boulder, CO (US)

(73) Assignees: Sumitomo Bakelite Company, Ltd., Tokyo (JP); Somalogic, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/306,240

(22) Filed: Nov. 29, 2011

(65) Prior Publication Data

US 2012/0070474 A1 Mar. 22, 2012

Related U.S. Application Data

(62) Division of application No. 11/908,170, filed as application No. PCT/US2006/008877 on Mar. 14, 2006, now Pat. No. 8,088,340.

(30) Foreign Application Priority Data

Mar. 15, 2005 (JP) ................................. 2005-072862

(51) Int. Cl.
*G01N 33/52* (2006.01)
(52) U.S. Cl. .... 422/420; 422/425; 525/54.1; 435/287.2; 435/287.7; 435/287.8
(58) Field of Classification Search .................. 422/420, 422/425; 525/54.1; 435/287.2, 287.7, 287.8
See application file for complete search history.

(56) References Cited

U.S. PATENT DOCUMENTS 7,629,029 B2 * 12/2009 Mao et al. .................. 427/372.2
8,088,340 B2 * 1/2012 Matsumoto et al. .......... 422/420

2002/0043499 A1 4/2002 Hammen et al.
2005/0048570 A1 3/2005 Weber et al.
2005/0202396 A1 9/2005 Ruhe

FOREIGN PATENT DOCUMENTS

| EP | 0 468 585 A2 | | 7/1991 |
|---|---|---|---|
| JP | 2001-116750 A | | 4/2001 |
| JP | 2004-531390 T | | 10/2004 |
| JP | 2005-008863 A | | 1/2005 |
| JP | 2005-010004 | * | 1/2005 |
| JP | 2006-322739 A | | 11/2006 |
| WO | 03/040700 A1 | | 5/2003 |
| WO | 2004/039854 A2 | | 5/2004 |

OTHER PUBLICATIONS

Y. Hayashizaki, et al; "Practical Manual of DNA Microarray", pp. 57, First Printing: Published on Dec. 1, 2000; Published by: Yodosha Co., Ltd.
Jongwon Park, et al; "Evaluation of 2-Methacryloyloxyethyl Phosphorylcholine Polymeric Nanoparticle for Immunoassay of C-Reactive Protein Detection", Analytical Chemistry, vol. 76, No. 9, May 1, 2004, pp. 2649-2655; XP-002311948.
USPTO NFOA mailed Sep. 16, 2010 in connection with U.S. Appl. No. 11/908,170.
USPTO NFOA mailed Apr. 28, 2011 in connection with U.S. Appl. No. 11/908,170.
USPTO NOA mailed Aug. 30, 2011 in connection with U.S. Appl. No. 11/908,170.
Supplementary European Search Report: EP 06 73 7993.
International Search Report mailed Nov. 28, 2006; PCT/US06/08877.

* cited by examiner

*Primary Examiner* — Jill Warden
*Assistant Examiner* — Monique Cole
(74) *Attorney, Agent, or Firm* — Ladas & Parry LLP

(57) ABSTRACT

A biochip substrate capable of realizing the high detection accuracy by restricting a nonspecific adsorption or bonding of a substance to be detected, when used for a detection or analysis of protein, nucleic acids and the like. The biochip substrate is for fixing a biologically active substance on a surface of a solid substrate, and characterized in that it has a layer comprising a polymer compound obtained by copolymerizing an ethylenically unsaturated polymerizable monomer having an alkylene glycol residue, an ethylenically unsaturated polymerizable monomer having a functional group for fixing a biologically active substance and an ethylenically unsaturated polymerizable monomer having a cross-linkable functional group, on the surface of the substrate.

12 Claims, No Drawings

POLYMER COMPOUND FOR BIOMEDICAL USE AND BIOCHIP SUBSTRATE USING SUCH A POLYMER COMPOUND

TECHNICAL FIELD

The present invention relates to a polymer compound for biomedical use having a function of fixing a biologically active substance. The present invention further relates to a surface coating material containing such a polymer compound, and relates to a biochip substrate using such a polymer compound.

BACKGROUND ART

Conventionally, various attempts to evaluate the genetic activity or decode the biological process including a disease process or a biological process of pharmacological effect have been focused on genomics. However, proteomics can provide further information about the biological function of cells. Proteomics includes qualitative and quantitative measurement of the gene activity by detecting and quantifying the expression on a protein level rather than a gene level. Proteomics also includes a study of events which are not coded for gene, such as a post-translational modification of protein and an interaction between proteins.

At the present, it is possible to obtain an enormous volume of genome information. Accordingly, there is an increasing demand for high throughput proteomics. DNA chips have been come into practical use, as molecular arrays for this purpose. On the other hand, in order to detect proteins which are the most complicated and the most variable in biological functions, there are proposed protein chips, which are enthusiastically studied in these days. Protein chip is a collective term used to refer to any device in which protein or a molecule for catching such a protein is fixed on a surface of a chip (a fine substrate or particle).

However, the protein chips at present are generally developed as an extension of DNA chips. Therefore, attempts are made in order to fix a protein or a molecule for catching such a protein on a surface of a chip such as glass substrate or particle (e.g. Japanese Patent Application Laid-open No. 2001-116750).

It is considered that a nonspecific adsorption of a substance to be detected onto a substrate is one reason of decreasing the S/N ratio in detecting signals of protein chips (e.g. Hayashizaki, Y. and Okazaki, K., 2000, "Sure to Get data: Practical Manual of DNA Microarray", pp. 57, Yodosha, Tokyo).

As a method of fixing proteins or the like, two methods are implemented at present. One is a fixing method based on a physical adsorption of protein. According to this method, adsorption preventing agents are coated in order to prevent a nonspecific adsorption of the secondary antibody after the protein is fixed. However, the ability of these agent for preventing the nonspecific adsorption is not sufficient. Furthermore, since the adsorption preventing agent is coated after the primary antibody is fixed, the coating is made on the fixed protein which prevents the reaction between the biochip and the secondary antibody. Thereby, there is a need for a biochip capable of restricting the nonspecific adsorption of biologically active substances without coating the adsorption preventing agent after the primary antibody is fixed.

In order to solve the problem above, there is a need for a biochip capable of restricting a nonspecific adsorption of biologically active substances. In the case that such a biochip is used, there is a problem that the protein or the molecule for catching the protein which is fixed on the substrate flows out in the washing process after the protein is caught, so that the signal is deteriorated. As one approach to the problem above, there is disclosed a method of coating an active component containing a functional group, a spacer group and a bonding group, a cross-liking component and a matrix-forming component on a support and curing them, so that a functional surface strongly bonded with the support can be formed on the support (e.g. Japanese Patent Application Kohyo (Laid-Open under national phase of PCT Application) No. 2004-531390). However, in this disclosed method, a curing of a low molecular component is proceeded on the support. Thereby, if the support is a plastic substrate, the support may be adversely warped or deformed. Furthermore, since a matrix is formed in the form of network, there are problems that the reaction of the functional group for fixing the biologically active substance may be adversely restricted, or that the reproducibility of the functional expression of the fixed biologically active substance is poor. Furthermore, the nonspecific adsorption is not always restricted sufficiently, because the protein infiltrated into the inside of the matrix is difficult to wash.

DISCLOSURE OF INVENTION

Problem to be Solved by the Invention

An object of the present invention is to provide a polymer compound for biomedical use, which has an excellent ability of fixing biologically active substances, and hardly adsorbs to proteins nonspecifically, and has a chemical and physical stability against dissolving or deteriorating in the washing process, and can be suitably coated also on a surface of plastic substrates, as well as to provide a biochip substrate with a high S/N ratio using such a polymer compound.

Means for Solving the Problem

The inventors have studied enthusiastically in order to develop a polymer compound for biomedical use having an excellent ability of fixing biologically active substances and capable of restricting a nonspecific adsorption to proteins. In the result, it was found that a polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group has an excellent ability of fixing biologically active substances, and hardly causes a nonspecific adsorption, and can be coated uniformly on a plastic substrate without warping or waving, so that such a polymer compound can be used suitably for biochips. From this finding, the inventors have been accomplished the present invention.

That is, the present invention is (1) a polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group, (2) a polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance, an ethylenically unsaturated polymerizable monomer (c) having a cross-linkable functional group and an ethylenically unsaturated polymerizable monomer (d) having an alkyl group, (3) the polymer compound for biomedical use according to (1) or (2), wherein the ethylenically unsaturated polymerizable monomer (a) having an alkylene glycol residue is a monomer represented by the following general formula [1],

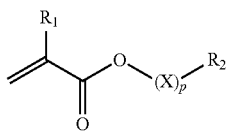

Formula [1]

wherein R1 is a hydrogen atom or a methyl group, R2 is a hydrogen atom or an alkyl group having 1 to 20 carbon atoms; X is an alkylene glycol residue having 1 to 10 carbon atoms; p is an integer from 1 to 100; in a case that p is an integer no less than 2 and no more than 100, the repeated X may be the same or may be different, (4) the polymer compound for biomedical use according to (1) or (2), wherein the ethylenically unsaturated polymerizable monomer (a) having an alkylene glycol residue is methoxypolyethylene glycol acrylate or methoxypolyethylene glycol methacrylate, (5) the polymer compound for biomedical use according to (4), wherein an average repeating number of the ethylene glycol residue of the methoxypolyethylene glycol acrylate or methoxypolyethylene glycol methacrylate is 3 to 100, (6) the polymer compound for biomedical use according to any one of (1) to (5), wherein the functional group of the ethylenically unsaturated polymerizable monomer (b) having a functional group for fixing a biologically active substance is at least one functional group selected from an aldehyde group, an active ester, an epoxy group, a vinyl sulfone group and biotin, (7) the polymer compound for biomedical use according to any one of (1) to (5), wherein the ethylenically unsaturated polymerizable monomer (b) having a functional group for fixing a biologically active substance is a monomer having an active ester represented by the following general formula [2],

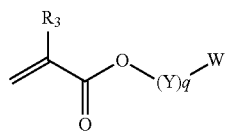

Formula [2]

wherein R3 is a hydrogen atom or a methyl group, Y is an alkyl group or an alkylene glycol residue having 1 to 10 carbon atoms; W is an active ester group; q is an integer from 1 to 20; in a case that q is an integer no less than 2 and no more than 20, the repeated Y may be the same or may be different, (8) the polymer compound for biomedical use according to (6) or (7), wherein the active ester is p-nitrophenyl ester or N-hydroxysuccinimide ester, (9) the polymer compound for biomedical use according to any one of (1) to (8), wherein the cross-linkable functional group of the ethylenically unsaturated polymerizable monomer (c) having a cross-linkable functional group is at least one functional group selected from an alkoxysilyl, epoxy, acryl and methacryl,

(10) the polymer compound for biomedical use according to any one of (1) to (8), wherein the ethylenically unsaturated polymerizable monomer (c) having a cross-linkable functional group is a monomer having an alkokysilyl represented by the following general formula [3],

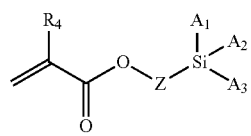

Formula [3]

wherein R4 is a hydrogen atom or a methyl group, Z is an alkyl group having 1 to 20 carbon atoms; at least one of A1, A2, A3 is hydrolyzable alkoxy group and the rest of A1, A2, A3 is/are alkyl group(s),

(11) the polymer compound for biomedical use according to any one of (2) to (10), wherein the ethylenically unsaturated polymerizable monomer (d) having an alkylene group is at least one monomer selected from n-butyl methacrylate, n-dodecyl methacrylate, n-octyl methacrylate, and cyclohexyl methacrylate,

(12) a surface coating material for biomedical use containing the polymer compound for biomedical use according to any one of (1) to (11),

(13) a biochip substrate obtained by forming a layer containing the polymer compound for biomedical use according to any one of (1) to (11) on a surface of a supporting substrate,

(14) the biochip substrate according to (13), wherein the supporting substrate is made of plastic,

(15) the biochip substrate according to (14), wherein the plastic is a saturated cyclic polyolefin,

(16) a method of manufacturing the biochip substrate according to any one of (13) to (15), including applying a solution containing the polymer compound for biomedical use according to any one of (1) to (11) onto a surface of a supporting substrate, and after the applying process, cross-linking the polymer compound,

(17) a biochip obtained by fixing a biologically active substance on the biochip substrate according to any one of (13) to (15),

(18) the biochip according to (17), wherein the biologically active substance is at least one biologically active substance selected from nucleic acid, aptamer, protein, oligopeptide, sugar chain and glycoprotein.

Effect of Invention

According to the present invention, it is possible to provide a polymer compound for biomedical use, which has an excellent ability of fixing biologically active substances, and hardly adsorbs to proteins nonspecifically, and has a chemical and physical stability against dissolving or deteriorating in the washing process, and can be suitably coated also on a surface of plastic substrates. It is also possible to provide a biochip substrate with a high S/N ratio using such a polymer compound.

BEST MODE FOR CARRYING OUT THE INVENTION

The polymer compound of the present invention is characterized in that it can be obtained by copolymerizing an ethylenically unsaturated polymerizable monomer (a) having an alkylene glycol residue, an ethylenically unsaturated polymerizable monomer (b) having a functional group for fixing a biologically active substance, and an ethylenically unsaturated polymerizable monomer (c) having a cross-linkable functional group. This polymer compound is a polymer having a nature of inhibiting a nonspecific adsorption of biologically active substances, a nature of fixing biologically active substances and a nature of cross-linking polymer chains. In this polymer compound, the alkylene glycol residue acts to inhibit the nonspecific adsorption of biologically active substances, and the functional group for fixing a biologically active substance acts to fix biologically active substances.

The ethylenically unsaturated polymerizable monomer (a) having an alkylene glycol residue to be used in the present invention is not limited to any special structure, but preferably may be a compound represented by the general formula [1] including a chain of (meth)acrylic group and alkylene glycol residue X having 1 to 10 carbon atoms. In the present application, the term "alkylene glycol residue" means an "alkyleneoxy group" (—R—O— wherein R is alkylene group) which remains after a condensation reaction of one or both end hydroxy groups of an alkylene glycol (HO—R—OH, wherein R is alkylene group) with other compounds. For example, "alkylene glycol residue" of methylene glycol (HO—CH$_2$—OH) is methyleneoxy group (—CH$_2$—O—), and "alkylene glycol residue" of ethylene glycol (HO—CH$_2$—CH$_2$—OH) is ethyleneoxy group (—CH$_2$—CH$_2$—O—).

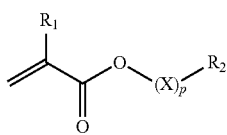

Formula [1]

In the formula [1], the carbon number of the alkylene glycol residue X is 1 to 10, preferably 1 to 6, more preferably 2 to 4, still more preferably 2 to 3, the most preferably 2. The repeating number p of the alkylene glycol residue is an integer from 1 to 100, preferably an integer from 2 to 100, more preferably an integer from 2 to 95, the most preferably an integer from 20 to 90. In the case that the repeating number is not less than 2 but not more than 100, the carbon numbers of the alkylene glycol residue X repeated in a chain may be the same or may be different.

Examples of the ethylenically unsaturated polymerizable monomer (a) having the alkylene glycol residue include: methoxypolyethyleneglycol(meth)acrylate; (meth)acrylates of an ester substituted by one hydroxy group such as 2-hydroxyethyl(meth)acrylate, 2-hydroxypropyl(meth)acrylate, and 2-hydroxybutyl(meth)acrylate; glycerolmono(meth)acrylate; (meth)acrylate having a polypropyleneglycol side chain; 2-methoxyethyl(meth)acrylate; 2-ethoxyethyl(meth)acrylate; methoxydiethyleneglycol(meth)acrylate; ethoxydiethyleneglycol(meth)acrylate; ethoxypolyethyleneglycol(meth)acrylate and so on. Among them, methoxypolyethyleneglycol methacrylate is preferable in view of availability. In the present invention, "(meth)acrylate" refers to methacrylate or acrylate.

The functional group of "the ethylenically unsaturated polymerizable monomer (b) having a functional group for fixing a biologically active substance" according to the present invention may be a chemically active group, receptor group, ligand group and so on, but not limited to them. Specific examples includes aldehyde group, activate ester, epoxy group, vinyl sulfone group, biotin, thiol group, amino group, isocyanate group, hydroxyl group, acrylate group, maleimide group, hydrazide group, azide group, amido group, sulfonate group, streptoavidin, metal chelate and so on, but not limited to them. Among them, aldehyde group, active ester, epoxy group and vinyl sulfone group are preferable, in view of the reactivity with the amino group which is much contained in biologically active substances, while biotin is preferable in view of its high coupling constant relative to biologically active substances. Particularly, active ester is the most preferable, in view of the storage stability of the monomer.

The ethylenically unsaturated polymerizable monomer (b) having a functional group for fixing a biologically active substance according to the present invention is not limited to any special structure, but may be preferably a compound represented by the following general formula [2] in which a (meth)acrylic group and an active ester group are bonded via an alkyl group or a chain of an alkylene glycol residue having 1 to 10 carbon atoms.

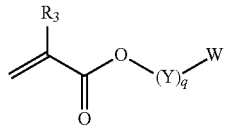

Formula [2]

In the formula [2], the carbon number of the alkylene glycol residue Y is 1 to 10, preferably 1 to 6, more preferably 2 to 4, still more preferably 2 to 3, the most preferably 2. The repeating number q of alkylene glycol residue Y is an integer from 1 to 20, preferably an integer from 2 to 18, more preferably an integer from 3 to 16, the most preferably an integer from 4 to 14. If the repeating number is not less than 2 and not more than 20, the carbon numbers of the alkylene glycol residues repeated in a chain may be the same or may be different.

The "active ester group" according to the present invention means an ester group activated relative to a nucleophilic reaction by having a high acidic electron attracting group as one substituent of the ester group, that is an ester group having a high reaction activity, which is conventionally used in various chemical synthesis such as in a field of polymer chemistry, or in a field of peptide synthesis. Practically, phenol esters, thiophenol esters, N-hydroxyamine esters or esters of heterocyclic hydroxy compound and so on are known as active ester groups each having a much higher activity than that of alkyl ester or the like.

Examples of such an active ester group include p-nitrophenyl active ester group, N-hydroxysuccinimide active ester group, succinimide active ester group, phthalic acid imide active ester group, 5-norbornene-2,3-dicarboxylmide active ester group and so on. Among them, p-nitrophenyl active ester group or N-hydroxysuccinimide active ester group is preferable, and p-nitrophenyl active ester group is the most preferable.

The preferable ratio of the ethylenically unsaturated polymerizable monomer (b) having a functional group for fixing a biologically active substance according to the present invention is 1 to 50 mol %, more preferably 1 to 30 mol %, the most preferably 1 to 20 mol %.

The ethylenically unsaturated polymerizable monomer (c) having a cross-linkable functional group according to the present invention is not limited to any special kind, insofar as the reaction of the cross-linkable functional group does not proceed during the synthesis of the polymer compound.

Examples of the cross-linkable functional group include a functional group generating a silanol group via hydrolysis, or epoxy group, (meth)acrylic group, glycidyl group and so on.

Among them, a functional group generating a silanol group via hydrolysis, or epoxy group and glycidyl group are preferable, in view of easy cross-linking process. Furthermore, a functional group generating a silanol group via hydrolysis is more preferable, in view of its cross-linking ability in a lower temperature environment.

The functional group generating a silanol group via hydrolysis means a group which is easily hydrolyzed and generates a silanol group, when it comes into contact with water. Examples of such a functional group include silyl halide group, alkoxy silyl group, phenoxy silyl group, acetoxy silyl group and so on. Among them, alkoxy silyl group, phenoxy silyl group and acetoxy silyl group are preferable, in view of halogen-free composition. Especially, alkoxy silyl group is the most preferable, in view of easily generating a silanol group.

Preferably, the ethylenically unsaturated polymerizable monomer having the functional group generating a silanol group via hydrolysis is an ethylenically unsaturated polymerizable monomer represented by the general formula [3] in which a (meth)acrylic group and an alkoxy silyl group are bonded to each other directly or via an alkyl chain having 1 to 20 carbon atoms.

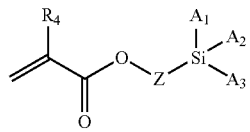

Formula [3]

Examples of the ethylenically unsaturated polymerizable monomer containing an alkoxy silyl group include a (meth)acryloxy alkyl silane compound such as 3-(meth)acryloxy propenyl trimethoxy silane, 3-(meth)acryloxy propyl bis(trimethyl siloxy)methyl silane, 3-(meth)acryloxy propyl dimethyl methoxy silane, 3-(meth)acryloxy propyl dimethyl ethoxy silane, 3-(meth)acryloxy propyl methyl dimetoxy silane, 3-(meth)acryloxy propyl methyl diethoxy silane, 3-(meth)acryloxy propyl trimethoxy silane, 3-(meth) acryloxy propil triethoxy silane, 3-(meth) acryloxy propyl tris (methoxyethoxy) silane, 8-(meth)acryloxy octanyl trimethoxy silane, 11-(meth)acryloxy undenyl trimethoxy silane and so on. Among them, 3-methacryloxy propyl trimethoxy silane, 3-methacryloxy propyl triethoxy silane, 3-metachryloxy propyl dimethyl methoxy silane and 3-methacryloxy propyl dimethyl ethoxy silane are preferable, in view of superior copolymerization ability relative to the ethylenically unsaturated polymerizable monomer having an alkylene glycol residue, or in view of the availability and so on. These ethylenically unsaturated polymerizable monomers each having an alkoxy silyl group may be used solely or as a combination of two or more kinds.

The preferable ratio of the ethylenically unsaturated polymerizable monomer (c) having a cross-linkable functional group according to the present invention is 1 to 20 mol %, more preferably 2 to 15 mol %, the most preferably 2 to 10 mol %.

The polymer compound according to the present invention may include another ethylenically unsaturated polymerizable monomer having a group other than the aforementioned group, in addition to the ethylenically unsaturated polymerizable monomer having an alkylene glycol residue, the ethylenically unsaturated polymerizable monomer having a functional group for fixing biologically active substance and the ethylenically unsaturated polymerizable monomer having a cross-linkable functional group. For example, an ethylenically unsaturated polymerizable monomer (d) having an alkyl group may be copolymerized. As such an ethylenically unsaturated polymerizable monomer (d) having an alkyl group, n-butyl methacrylate, n-dodecyl methacrylate or n-octyl methacrylate is preferable.

A method of synthesizing the polymer compound of the present invention is not limited to any special method. From the viewpoint of easiness in the synthesis, however, it may be preferably a method of conducting a radical polymerization of a mixture containing, at least, the ethylenically unsaturated polymerizable monomer (a) having an alkylene glycol residue, the ethylenically unsaturated polymerizable monomer (b) having a functional group for fixing a biologically active substance, and the ethylenically unsaturated polymerizable monomer (c) having a cross-linkable group, under the existence of a polymerization initiator, in solvent.

The solvent is not limited to any special solvent insofar as is each ethylenically unsaturated polymerizable monomer can be dissolved therein, but may be methanol, ethanol, t-butyl alcohol, benzene, toluene, tetrahydrofuran, dioxane, dichloromethane, chloroform and so on. These solvents may be used solely, or may be used as a combination of two or more kinds. In the case that the polymer compound is applied onto a plastic substrate, ethanol or methanol is preferable, in view of avoiding the denaturation of the substrate.

The polymerization initiator may be any usual radical initiator, including azo compounds such as 2,2'-azobisisobutylonitrile (hereinafter abbreviated as AIBN) and 1,1'-azobis (cyclohexane-1-carbonitrile); and organic peroxides such as benzoyl peroxide and lauryl peroxide; and so on.

The chemical structure of the polymer compound of the present invention is not limited to any special structure insofar as the polymer compound is a copolymer obtained by copolymerizing at least the ethylenically unsaturated polymerizable monomers each having an alkylene glycol residue, a functional group for fixing a biologically active substance and a cross-linkable functional group, regardless of copolymer type such as random copolymer, block copolymer and graft copolymer type.

The molecular weight of the polymer compound of the present invention is preferably not less than 5000, more preferably not less than 10000, on the basis of number-average molecular weight, in view of easiness in the purification by separating the polymer compound from the unreacted ethylenically unsaturated polymerizable monomers.

Owing to the polymer compound of the present invention, it is easy to provide a nature of restricting a nonspecific adsorption of biologically active substances, and a nature of fixing a specific biologically active substance, by coating a surface of a supporting substrate with the polymer compound. Furthermore, since the polymer compound of the present invention has a nature of cross-linking a plurality of polymer main chains, the cross-linking can be caused after the surface of the supporting substrate is coated. Thereby, the polymer compound on the substrate can have insolubility, so that signal degradation due to the supporting substrate washing can be reduced.

The coating of the polymer compound onto the surface of the supporting substrate may be achieved by the steps including (i) preparing a polymer compound solution which is obtained by dissolving a polymer compound in an organic solvent so that the concentration becomes 0.05 to 10 weight percent, (ii) applying the polymer compound solution onto the surface of the supporting substrate by a known process such as dipping or blowing, and (iii) then drying the applied solution in a room temperature environment or in a heated temperature environment. After that, a plurality of polymer main chains is cross-linked by any method suitable for a cross-linkable functional group. As for the polymer compound coating in the case that the cross-linkable functional group is a functional group which generates a silanol group via hydrolysis, a mix solution obtained by containing water in an organic solvent may be used. The contained water causes a hydrolysis, by which a silanol group is generated in the synthesized polymer. Furthermore, by heating the synthesized polymer, a plurality of main chains is bonded, so that the polymer compound becomes insoluble. From the viewpoint of easiness in preparation of the solution, the water content can be about 0.01 to 15 weight percent.

The organic solvent may be a simple solvent such as ethanol, methanol, t-butyl alcohol, benzene, toluene, tetrahydrofuran, dioxane, dichloromethane, chloroform, acetone, methylethylketone or the like, or may be a solvent mixture thereof. Particularly, ethanol and methanol are preferable, because they do not cause denaturation of the plastic substrate, and they are easy to dry. Furthermore, ethanol and methanol are preferable, because they can be mixed with water at a desirable ratio when the polymer compound is to be hydrolyzed in the solution.

In the drying process after the solution in which the polymer compound of the present invention is dissolved is applied onto the surface of the supporting substrate, the silanol groups in the polymer compound generate cross-linkings by condensing with silanol groups, hydroxy groups, amino groups and so on in another polymer compound so as to dehydrate water. Furthermore, also in the case that hydroxy groups, carbonyl groups, amino groups and so on exist on the surface of the supporting substrate, the condensation with dehydration is caused, so that a chemical bond with the surface of the supporting substrate can be made. Since the covalent bond which is formed by the condensation of the silanol group with dehydration is hardly hydrolyzed in its nature, the polymer compound coated on the surface of the supporting substrate hardly dissolves, or hardly detaches from the supporting substrate. The condensation of the silanol group with dehydration is accelerated by a heat treatment. A temperature range in which the polymer compound is not thermally denaturated is preferable. For example, a heat treatment is preferably performed in a temperature range from 60 to 120 t, for a time range from 5 minutes to 24 hours.

A material for the biochip substrate to be used in the present invention may be glass, plastic, metal and other materials, but plastic is preferable, in view of easiness in the surface treatment and the mass productivity. Thermoplastic is more preferable.

As the thermoplastic, a less fluorescent thermoplastic is preferable. For example, a linear polyolefin such as polyethylene or polypropylene; a cyclic polyolefin; fluorine-contained resin and so on are preferably used. Particularly, saturated cyclic polyolefin is more preferably used, because of its excellency in heat resistance, chemical resistance, low fluorescence and moldability. In this context, the saturated cyclic polyolefin means a saturated polymer obtained by hydrogenating a simple polymer having a cyclic olefin structure or by hydrogenating a copolymer of a cyclic olefin and an α-olefin.

In order to improve adhesiveness between the surface of the supporting substrate and the polymer compound coated thereon, it is preferable to activate the surface of the supporting substrate. An activating method may be a method of conducting a plasma treatment under a condition such as oxygen atmosphere, argon atmosphere, nitrogen atmosphere, or air atmosphere, or may be a method of conducting a treatment with excimer laser such as ArF or KrF. Particularly, the method of conducting a plasma treatment in an oxygen atmosphere is preferable.

By applying the polymer compound of the present invention onto the supporting substrate, it is possible to produce a biochip substrate capable of restricting nonspecific adsorption of biologically active substances. Furthermore, by cross-linking the polymer compound, it is possible to provide the insolubility to the polymer compound on the supporting substrate. Thus, the supporting substrate coated by the polymer compound can be suitably used for a biochip use.

By using the biochip substrate of the present invention, various biologically active substances can be fixed. The biologically active substance to be fixed may be nucleic acid, aptamer, protein, oligopeptide, sugar chain, glycoprotein and so on. For example, in the case that nucleic acid is to be fixed, it is preferable to introduce amino group in order to improve the reactivity with active ester group. An introduction position where the amino group is to be introduced may be an end of a molecular chain or may be a side chain (also called "branch"). However, it is preferable that the amino group is introduced at an end of a molecular chain.

In the present invention, in order to fix biologically active substances on the biochip substrate, a method of attaching a droplet of the solution or dispersion of biologically active substances is preferable.

After attaching the droplet, the biochip substrate is left at rest, so that the biologically active substance is fixed. For example, in the case that aminated nucleic acid is used, it is possible to fix the aminated nucleic acid by leaving it at rest for 1 hour at a temperature in a range from a room temperature to 80° C. The higher process temperature is preferable. The liquid in which the biologically active substance is dissolved or dispersed is preferably alkaline.

After washing, functional groups on a part of the surface of the biochip substrate other than a part where the biologically active substance is fixed are inactivated. The inactivation is preferably conducted with an alkali compound or a compound having a primary amino group in the case of active ester or aldehyde group.

Examples of the alkali compound which can be preferably used include sodium hydroxide, potassium hydroxide, sodium carbonate, sodium hydrogencarbonate, sodium dihydrogen phosphate, calcium hydroxide, magnesium hydroxide, sodium borate, lithium hydroxide, potassium phosphate and so on.

Examples of the compound having a primary amino group which can be preferably used include methyl amine, ethyl amine, butyl amine, glycine, 9-aminoaquagene, aminobutanol, 4-aminobutyric acid, aminocaprylic acid, aminoethanol, 5-amino-2,3-dihydro-1,4-pentanol, aminoethanethiol hydrochloride, aminoethanethiol sulfuric acid, 2-(2-aminoethylamino)ethanol, 2-aminoethyl dihydrogen phosphate, aminoethyl hydrogensulfate, 4-(2-aminoethyl) morpholine, 5-aminofluorescein, 6-aminohexanoic acid, aminohexyl cellulose, p-aminohippuric acid, 2-amino-2-hydroxymethyl-1, 3-propane diol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, aminosalicylic acid, aminoquinoline, 4-aminophthalonitrile, 3-aminophthalimide, p-aminopropiophenone, aminophenyl acetic acid, aminonaphthalene and so on. Particularly, aminoethanol and glycine are the most preferable.

The biochip thus obtained by fixing the biologically active substance can be used for various analysis systems including an immunodiagnosis system, a gene microarray system, a protein microarray system, and a microfluidic device.

EXAMPLES

<Synthesis of p-nitrophenyloxycarbonyl-polyethylene glycol methacrylate (MEONP)>

0.01 mol of polyethylene glycol monomethacrylate (Blenmer PE-200 (n=4) available from NOF CORPORATION) was dissolved into 20 mL of chloroform. After that, the solution was cooled to −30° C. While the solution temperature was maintained at −30° C., a homogeneous solution which was already made in advance from 0.01 mol of p-nitrophenyl chloroformate (available from Aldrich), 0.01 mol of triethylamine (available from Wako Pure Chemical Industries, Ltd.) and 20 mL of chloroform was slowly dropped into the former solution maintained at −30° C. After the reaction at −30° C. for 1 hour, the solution was stirred for another 2 hours. After that, salt was removed from the reaction liquid via filteration, and the solvent was removed so that p-nitrophenyloxycarbonyl-polyethylene glycol methacrylate (MEONP) was obtained. The obtained monomer was characterized with $^1$H-NMR (in heavy chloroform solvent). In the result, it was confirmed that 4.5 units of ethylene glycol residue were contained.

Synthesis Example 1 of Polymer Compound

Polyethylene glycol methylether methacrylate (also known as methoxypolyethylene glycol methacrylate) (PEGMA, number-average molecular weight Mn=about 188, available from Aldrich), p-nitrophenyloxycarbonyl-polyethylene glycol methacrylate (MEONP), and 3-methacryloxypropyldimethylethoxy silane (MPDES available from GELEST, INC.) were dissolved in dehydrated ethanol, so as to prepare a monomer mixture solution in which the concentration of each ingredient was 0.90 mol/L, 0.05 mol/L and 0.05 mol/L, respectively in this order. Furthermore, 0.002 mol/L of 2,2-azobisisobutyronitrile (AIBN available from Wako Pure Chemical Industries, Ltd.) was added to the monomer mixture solution, and the monomer mixture solution was stirred until a homogeneous solution was obtained. After that, the reaction was conducted for 4 hours at 60° C.' in an argon gas atmosphere, the reaction solution was dropped into diethylether, and the precipitation was collected. The obtained polymer compound was measured with 1H-NMR (in heavy chloroform solvent). From integral values of a peak appeared around 0.13 ppm and characterized as a methyl group bonded to Si of MPDES, a peak appeared around 3.4 ppm and characterized as an end methoxy group of PEGMA, and a peak appeared around 7.4 ppm and 8.29 ppm and characterized as a benzene ring of MEONP, the composition ratio of the polymer compound was calculated. The result was shown in Table 1.

Synthesis Example 2 of Polymer Compound

Polyethylene glycol methylether methacrylate (also known as methoxypolyethylene glycol methacrylate) (PEGMA, number-average molecular weight Mn=about 300, available from Aldrich), p-nitrophenyloxycarbonyl-polyethylene glycol methacrylate (MEONP), and 3-methacryloxypropyldimethylethoxy silane (MPDES available from GELEST, INC.) were dissolved in dehydrated ethanol, so as to prepare a monomer mixture solution in which the concentration of each ingredient was 0.90 mol/L, 0.05 mol/L and 0.05 mol/L, respectively in this order. Furthermore, 0.01 mol/L of 2,2-azobisisobutyronitrile (AIBN available from Wako Pure Chemical Industries, Ltd.) was added to the monomer mixture solution, and the monomer mixture solution was stirred until a homogeneous solution was obtained. After that, the reaction was conducted for 2 hours at 60° C. in an argon gas atmosphere, the reaction solution was dropped into diethylether, and the precipitation was collected. The obtained polymer compound was measured with 1H-NMR (in heavy chloroform solvent). From integral values of a peak appeared around 0.13 ppm and characterized as a methyl group bonded to Si of MPDES, a peak appeared around 3.38 ppm and characterized as an end methoxy group of PEGMA, and a peak appeared around 7.4 ppm and 8.3 ppm and characterized as a benzene ring of MEONP, the composition ratio of the polymer compound was calculated. The result was shown in Table 1.

Synthesis Example 3 of Polymer Compound

Polyethylene glycol methylether methacrylate (also known as methoxypolyethylene glycol methacrylate) (PEGMA, number-average molecular weight Mn=about 475, available from Aldrich), p-nitrophenyloxycarbonyl-polyethylene glycol methacrylate (MEONP), and 3-methacryloxypropyldimethylethoxy silane (MPDES available from GELEST, INC.) were dissolved in dehydrated ethanol, so as to prepare a monomer mixture solution in which the concentration of each ingredient was 0.90 mol/L, 0.05 mol/L and 0.05 mol/L, respectively in this order. Furthermore, 0.002 mol/L of 2,2-azobisisobutyronitrile (AIBN available from Wako Pure Chemical Industries, Ltd.) was added to the monomer mixture solution, and the monomer mixture solution was stirred until a homogeneous solution was obtained. After that, the reaction was conducted for 1.5 hours at 60° C. in an argon gas atmosphere, the reaction solution was dropped into diethylether, and the precipitation was collected. The obtained polymer compound was measured with 1H-NMR (in heavy ethanol solvent). From integral values of a peak appeared around 0.15 ppm and characterized as a methyl group bonded to Si of MPDES, a peak appeared around 3.35 ppm and characterized as an end methoxy group of PEGMA, and a peak appeared around 7.6 ppm and 8.4 ppm and characterized as a benzene ring of MEONP, the composition ratio of the polymer compound was calculated. The result was shown in Table 1.

Synthesis Example 4 of Polymer Compound

Polyethylene glycol methylether methacrylate (also known as methoxypolyethylene glycol methacrylate) (PEGMA, number-average molecular weight Mn=about 1100, available from Aldrich), p-nitrophenyloxycarbonyl-polyethylene glycol methacrylate (MEONP), and 3-methacryloxypropyldimethylethoxy silane (MPDES available from GELEST, INC.) were dissolved in dehydrated ethanol, so as to prepare a monomer mixture solution in which the concentration of each ingredient was 0.45 mol/L, 0.025 mol/L and 0.025 mol/L, respectively in this order. Furthermore, 0.002 mol/L of 2,2-azobisisobutyronitrile (AIBN available from Wako Pure Chemical Industries, Ltd.) was added to the monomer mixture solution, and the monomer mixture solution was stirred until a homogeneous solution was obtained. After that, the reaction was conducted for 1 hour at 60° C. in an argon gas atmosphere, the reaction solution was dropped into diethylether, and the precipitation was collected. The obtained polymer compound was measured with $^1$H-NMR (in heavy ethanol solvent). From integral values of a peak appeared around 0.16 ppm and characterized as a methyl group bonded to Si of MPDES, a peak appeared around 3.35 ppm and characterized as an end methoxy group of PEGMA, and a peak appeared around 7.6 ppm and 8.4 ppm and characterized as a benzene ring of MEONP, the composition ratio of the polymer compound was calculated. The result was shown in Table 1.

TABLE 1

|  |  | Synthesis Example 1 | Synthesis Example 2 | Synthesis Example 3 | Synthesis Example 4 |
|---|---|---|---|---|---|
| Feed Composition Ratio (mol %) | PEGMA(188) | 90 | 0 | 0 | 0 |
|  | PEGMA(300) | 0 | 90 | 0 | 0 |
|  | PEGMA(475) | 0 | 0 | 90 | 0 |
|  | PEGMA(1100) | 0 | 0 | 0 | 90 |
|  | MEONP | 5 | 5 | 5 | 5 |
|  | MPDES | 5 | 5 | 5 | 5 |
| Composition Ratio obtained from 1H-NMR (mol %) | PEGMA(188) | 92 | 0 | 0 | 0 |
|  | PEGMA(300) | 0 | 92 | 0 | 0 |
|  | PEGMA(475) | 0 | 0 | 91 | 0 |
|  | PEGMA(1100) | 0 | 0 | 0 | 92 |
|  | MEONP | 3 | 3 | 4 | 3 |
|  | MPDES | 5 | 5 | 5 | 5 |

Examples 1-4

A saturated cyclic polyolefin resin (MFR (Melt Flow Rate) was 21 g/10 min., hydrogenation ratio was substantially 100%, thermal deformation temperature was 123° C.), obtained via ring-opening polymerization of 5-methyl-2-norbornene and hydrogenation the polymerized product, was formed into a slide glass shape (dimension: 76 mm×26 mm×1 mm) via injection molding, so that a solid phase substrate was made as a supporting substrate. The surface of the substrate was oxidized by a plasma process in an oxygen atmosphere. This solid substrate was dipped into a 0.3 weight percent ethanol solution of each polymer compound obtained by the synthesis examples 1 to 4, and heated and dried for 4 hours at 65° C., so that a layer containing a polymer compound comprising an ethylenically unsaturated polymerizable monomer having an alkylene glycol residue, an ethylenically unsaturated polymerizable monomer having an active ester group and an ethylenically unsaturated polymerizable monomer having a cross-linkable functional group was introduced on the surface of the solid phase substrate.

Comparative Example 1

(Non-coated Substrate)

A saturated cyclic polyolefin resin (MFR (Melt Flow Rate) was 21 g/10 min., hydrogenation ratio was substantially 100%, thermal deformation temperature was 123° C.), obtained via ring-opening polymerization of 5-methyl-2-norbornene and hydrogenation the polymerized product, was formed into a slide glass shape (dimension: 76 mm×26 mm×1 mm) via injection molding, so that a solid phase substrate was made. The surface of the substrate was oxidized by a plasma process in an oxygen atmosphere.

Comparative Example 2

(Aldehyde-coated Substrate)

A saturated cyclic polyolefin resin (MFR (Melt Flow Rate) was 21 g/10 min, hydrogenation ratio was substantially 100%, thermal deformation temperature was 123° C.), obtained via ring-opening polymerization of 5-methyl-2-norbornene and hydrogenation the polymerized product, was formed into a slide glass shape (dimension: 76 mm×26 mm×1 mm) via injection molding, so that a solid phase substrate was made. The surface of the substrate was oxidized by a plasma process in an oxygen atmosphere. This solid substrate was dipped into a 2 volume percent ethanol solution of 3-aminopropylmethoxy silane. After that, the substrate was washed by pure water, and heated for 2 hours at 45° C. so as to introduce amino group. Furthermore, the substrate was dipped into 1 volume percent aqueous solution of glutaraldehyde, and then washed by pure water, so that aldehyde group was introduced.

Comparative Example 3

An amine-reactive slide glass substrate was made according to Example X in Japanese Patent Application Kohyo (Laid-Open under national phase of PCT Application) No. 2004-531390.

As for substrates obtained in Examples 1 to 4 and Comparative Example 3, the following experiment was repeated 5 times so as to evaluate the reproducibility. The reproducibility was evaluated in a system where a mouse IgG2a as antigen was not added.

Experiment 1

Process 1 (Fixation of Primary Antibody)

Next, a sandwich method was conducted on the substrates obtained in. Examples and Comparative Examples. In detail, firstly, anti-mouse IgG2a as primary antibody controlled at 3.3 mol/L with carbonic acid buffer (pH=9.5, available from Wako Pure Chemical Industries, Ltd.) was spotted on each substrate by an automatic spotter. After that, each substrate was left at rest for 24 hours in a room temperature environment, so that the primary antibody was fixed.

Process 2 (Adsorption Preventing Treatment)

After that, each substrate according to Examples 1 to 4 was dipped into an aqueous solution (pH=9.5) of 0.1 mol/L ethanol amine (available from Wako Pure Chemical Industries, Ltd., ultrapure grade) and 0.1 mol/L tris buffers (available from SIGMA) for 1 hour, so that the residual active ester part was deactivated. On the other hand, one substrate according to Comparative Example 1 was subjected to the adsorption preventing treatment by dipping it into a quadruple dilution of a commercially available anti-adsorption agent, "block ace" (available from Dainippon Pharma Co., Ltd.), for 2 hours, in which PBS buffer (available from Nissui Pharma Co., Ltd.: a buffer obtained by dissolving 9.6 g of Dulbecco PBS (−) for culturing tissue into 1 L of pure water) was used as the diluent. Another substrate according to Comparative Example 1 was prepared without the adsorption preventing treatment. The substrate according to Comparative Example 2 was subjected to the adsorption preventing treatment by dipping it into a quadruple dilution of the commercially available anti-adsorption agent, "block ace" (available from Dainippon Pharma Co., Ltd.), for 2 hours, in which PBS buffer (available from Nissui Pharma Co., Ltd.: a buffer obtained by dissolving 9.6 g of Dulbecco PBS (−) for culturing tissue into 1 L of pure water) was used as the diluent.

Process 3 (Antigen-Antibody Reaction 1)

After that, a FBS (Fetal Bovine Serum) solution was prepared by diluting to 10% with PBS buffer (available from Nissui Pharma Co., Ltd.: a buffer obtained by dissolving 9.6 g of Dulbecco PBS (−) for culturing tissue into 1 L of pure water). Into this solution, the mouse IgG2a as antigen was added, so that 20 nmol/L solution was prepared. This solution was diluted with 10% FBS solution, which was diluted with PBS buffer (available from Nissui Pharma Co., Ltd.: a buffer obtained by dissolving 9.6 g of Dulbecco PBS (−) for culturing tissue into 1 L solvent), so that 1 time diluted, 2 times diluted, 3 times diluted and 4 times diluted solutions were prepared. Antigen-antibody reactions were conducted by bringing these diluted solutions, as well as 10% FBS solution containing no IgG2a, into contact with each substrate for 2 hours at 37° C. After the antigen-antibody reactions, the substrates were washed, for 5 minutes at a room temperature, with 1×SSC buffer (obtained by diluting SSC20× buffer available from Zymed Laboratories, Inc.) to which 0.05 wt % non-ionic surfactant, "Tween 20" (available from Roche Diagnostics K.K.) was added.

Process 4 (Antigen-Antibody Reaction 2)

After washing, biotin-labeled anti-mouse IgG2a as secondary antibody was added to PBS buffer (available from Nissui Pharma Co., Ltd.: a buffer obtained by dissolving 9.6 g of Dulbecco PBS (−) for culturing tissue into 1 L of pure water), so that 20 nmol/L solution was prepared. Antigen-antibody reactions were conducted by bringing each substrate into contact with this solution for 2 hours at 37° C. After antigen-antibody reaction, the substrates were washed, for 5 minutes at a room temperature, with 1×SSC buffer (obtained by diluting SSC20×buffer available from Zymed Laboratories, Inc.) to which 0.05 wt % non-ionic surfactant, "Tween 20" (available from Roche Diagnostics K.K.) was added.

Process 5 (Labeling)

At the last, Cy5-labeled streptavidin was added to PBS buffer (available from Nissui Pharma Co., Ltd.: a buffer obtained by dissolving 9.6 g of Dulbecco PBS (−) for culturing tissue into 1 L of pure water), so that 20 nmol/L solution was prepared. Reactions were conducted by bringing each substrate into contact with this solution for 30 minutes at 37° C. After that, each substrate was washed, for 5 minutes at a room temperature, with 1×SSC buffer (obtained by diluting SSC20×buffer available from Zymed Laboratories, Inc.) to which 0.05 wt % non-ionic surfactant, "Tween 20" (available from Roche Diagnostics K.K.) was added, so that each substrate was labeled.

Fluorescent amount measurement was conducted about each substrate, so that each spot signal intensity value and each background value were evaluated. The result of the background value was shown in Table 2, the result of the spot signal intensity value was shown in Table 3, and the result of the reproducibility test was shown in Table 4.

Each measurement of the fluorescent amount in Examples and Comparative Examples was conducted by means of a microarray scanner, "ScanArray" (available from Packard BioChip Technologies). As for measurement conditions, the laser power was 90%, the PMT sensitivity was 50%, the excitation wavelength was 649 nm, the measurement wavelength was 670 nm and the resolution was 50μm.

By comparing Examples 1 to 4 with Comparative Example 1 (without block ace treatment), it was observed that background values were reduced in the biochip substrates according to the present invention.

Also, by comparing Examples 1 to 4 with Comparative Example 2, it was understood that the biochip substrates according to the present invention have the lower background values and the higher signal intensity values, in comparison with a case that a conventional aldehyde substrate was treated with a commercially available anti-adsorption agent.

By comparing Examples 1 to 4 with Comparative Example 3, it was understood that the biochip substrates according to the present invention have the lower background values than that of the substrate according to Japanese Patent Application Kohyo (Laid-Open under national phase of PCT Application) No. 2004-531390. It means that nonspecific protein contained in serum hardly adheres to the biochip substrates according to the present invention. Also, it was understood that the biochip substrates according to the present invention have the lower signal intensity value of the primary antibody spotted part without any antigen. It means that the primary antibody is fixed on the substrate in a condition that the antibody function thereof is active. Also, it was understood that the biochip substrates according to the present invention exhibit the excellent reproducibility.

TABLE 2

Background Value

| | Block Ace Treatment | Background Value |
|---|---|---|
| Example 1 | | 723 |
| Example 2 | | 837 |
| Example 3 | | 814 |
| Example 4 | | 459 |
| Comparative Example 1 | Treated | 5,610 |
| Comparative Example 1 | Not treated | 22,406 |
| Comparative Example 2 | Treated | 3,025 |
| Comparative Example 3 | | 1200 |

TABLE 3

Signal Intensity Value

| | Block Ace Treatment | Dilution Factor | | | | Without Antigen |
|---|---|---|---|---|---|---|
| | | 1 | 2 | 3 | 4 | |
| Example 1 | | 28,001 | 13,505 | 7,903 | 6,040 | 901 |
| Example 2 | | 27,003 | 12,901 | 8,401 | 6,201 | 889 |
| Example 3 | | 29,301 | 12,001 | 7,001 | 5,809 | 814 |
| Example 4 | | 27,022 | 13,901 | 8,999 | 6,901 | 501 |
| Comparative Example 1 | Treated | 15049 | 13049 | 10494 | 9122 | 8720 |
| Comparative Example 1 | Not treated | ND | ND | ND | ND | ND |
| Comparative Example 2 | Treated | 16,901 | 110,01 | 6,914 | 4,502 | 3,025 |
| Comparative Example 3 | | 14,025 | 8,002 | 4585 | 3046 | 2901 |

ND means "not detectable".

TABLE 4

Reproducibility (without antigen)

| | | $1^{st}$ | $2^{nd}$ | $3^{rd}$ | $4^{th}$ | $5^{th}$ |
|---|---|---|---|---|---|---|
| Example 1 | Background Value | 723 | 748 | 825 | 650 | 722 |
| | Signal Intensity Value | 901 | 882 | 910 | 820 | 842 |
| Example 2 | Background Value | 837 | 805 | 750 | 892 | 853 |
| | Signal Intensity Value | 889 | 841 | 849 | 923 | 904 |
| Example 3 | Background Value | 814 | 890 | 614 | 833 | 854 |
| | Signal Intensity Value | 814 | 923 | 702 | 850 | 994 |
| Example 4 | Background Value | 459 | 502 | 403 | 555 | 433 |
| | Signal Intensity Value | 501 | 552 | 502 | 639 | 488 |

TABLE 4-continued

Reproducibility (without antigen)

|  |  | 1st | 2nd | 3rd | 4th | 5th |
|---|---|---|---|---|---|---|
| Comparative Example 3 | Background Value | 1200 | 2003 | 1039 | 2599 | 1874 |
|  | Signal Intensity Value | 2901 | 4432 | 2901 | 5045 | 6494 |

As for the substrate of Example 4 and the substrate of Comparative Example 3, the following experiments 2 to 6 were conducted for further evaluations.

Experiment 2

Process 1 (Fixation of Aptamer)

Next, onto the substrates obtained in Example 4 and Comparative Example 3, various aptamer solutions each prepared so as to be 10 μmol/L solution with 0.1 M phosphate buffer (pH=9.5, available from Wako Pure Chemical Industries, Ltd.) were spotted on the same substrate. Aptamers for detecting endostatin, bFGF, and VEGF were used. After that, the substrates were left at rest for 1 hour at 65° C., so that each aptamer was fixed.

Process 2 (Adsorption Prevention Treatment)

After that, the substrates were dipped into an aqueous solution (pH=9.5) of 0.1 mol/L ethanol amine (available from Wako Pure Chemical Industries, Ltd., ultrapure grade) and 0.1 mol/L tris buffers ("T5912" available from SIGMA) for 1 hour, so that the residual active ester part was deactivated.

Process 3 (Reaction of Aptamer with Protein)

After that, endostatin ("SP5230CP" available from Acris Antibody GmgH) solution was prepared by diluting it to 1 μg/mL with an aqueous solution of 40 mM HEPES buffer ("GB60" available from DOJINDO LABORATORIES, 01=7.5), 111 mM sodium chloride, 5 mM potassium chloride, 1 mM magnesium chloride and 1 mM calcium chloride. This solution was brought into contact with the substrates for 2 hours at 37° C., so that the reaction between aptamer and protein was conducted. After the reaction, the substrates were washed with an aqueous solution of 40 mM HEPES buffer (pH=7.5), 111 mM sodium chloride, 5 mM potassium chloride, 1 mM magnesium chloride, 1 mM calcium chloride and 0.1% sodium dodecyl sulfate, for 30 minutes at 37° C.

Process 4 (Staining Process)

After washing, the substrates were brought into reaction with a solution prepared by containing 3 mg/mL NHS-ALEXA 647 (available from Molecular Probe) in 0.1M carbonic acid buffer (pH=9.0) solution, for 30 minutes at a room temperature. After the reaction, the substrates were washed with SSPE buffer ("S1027" available from SIGMA, pH=7.5) containing 0.1% sodium dodecyl sulfate, for 5 minutes at a room temperature.

Experiment 3

An experiment the same as Experiment 2 was conducted except that FGF basic ("PA055X" available from Acris Antibody GmbH) was used instead of endostatin used in Process 3 of Experiment 2.

Experiment 4

An experiment the same as Experiment 2 was conducted except that VEGF ("293-VE-010" available from R&D System Inc.) was used instead of endostatin used in Process 3 of Experiment 2.

Experiment 5

An experiment the same as Experiment 2 was conducted except that human serum AB type ("29319-49" available from Dainippon. Pharma Co., Ltd.) solution diluted to 10% was used instead of endostatin solution used in Process 3 of Experiment 2.

(Experiment 6

An experiment the same as Experiment 2 was conducted except that human serum AB type ("29319-49" available from Dainippon Pharma Co., Ltd.) solution diluted to 10% and VEGF ("293-VE-010" available from R&D System Inc.) diluted to 10 μg/mL were used as a single solution, instead of endostatin solution used in Process 3 of Experiment 2.

Fluorescent amount measurement was conducted for each Experiment, so that the spot signal intensity value and the background value were evaluated.

Each measurement of the fluorescent amount was conducted by means of a microarray scanner, "ScanArray" (available from Packard BioChip Technologies). As for measurement conditions, the laser power was 90%, the PMT sensitivity was 50%, the excitation wavelength was 649 nm, the measurement wavelength was 670 nm and the resolution was 50 μm.

The evaluation result of Experiments 2 to 6 using the substrate of Example 4 was shown in Table 5, and the evaluation result of Experiments 2 to 6 using the substrate of Comparative Example 3 was shown in Table 6.

As for the substrate of Example 4, a specific signal of protein reacted with the fixed aptamer was observed in Experiments 2 to 4. In Experiment 5, each protein in serum was detected, and the low background values were maintained.

As for the substrate of Comparative Example 3, although a specific protein and fixed aptamer were detected, background values were high in Experiments 2 to 4. In experiments 5 and 6, although the signal values were high, any effect of adding VEGF was not detected as a signal. As this reason, it is considered that the signal was high because the aptamer recognizes not only the specific protein but also other protein nonspecifically. Furthermore, since the serum was used, the protein was adsorbed to the substrate, so that the background values become high.

TABLE 5

Result of Experiments 2-4 using Substrate of Example 1

|  | Signal of endostatin aptamer | Signal of bFGF aptamer | Signal of VEGF aptamer | Background Value |
|---|---|---|---|---|
| Experiment 2 | 10450 | 103 | 84 | 78 |
| Experiment 3 | 85 | 9740 | 78 | 75 |
| Experiment 4 | 90 | 89 | 5022 | 74 |
| Experiment 5 | 5340 | 1024 | 482 | 82 |
| Experiment 6 | 5420 | 1003 | 4984 | 8 |

TABLE 6

Result of Experiments 2-6 using Substrate of Comparative Example 3

| | Signal of endostatin aptamer | Signal of bFGF aptamer | Signal of VEGF aptamer | Background Value |
|---|---|---|---|---|
| Experiment 2 | 11576 | 587 | 605 | 803 |
| Experiment 3 | 594 | 9794 | 521 | 905 |
| Experiment 4 | 742 | 684 | 5823 | 840 |
| Experiment 5 | 16843 | 13854 | 11538 | 1024 |
| Experiment 6 | 15923 | 12784 | 12424 | 1114 |

The invention claimed is:

1. A polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group, wherein the ethylenically unsaturated polymerizable monomer (c) having a cross-linkable functional group is a monomer having an alkoxysilyl represented by the following general formula [3],

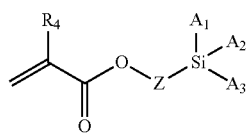

Formula [3]

wherein $R_4$ is a hydrogen atom or a methyl group, Z is an alkyl group having 1 to 20 carbon atoms; at least one of $A_1$, $A_2$, $A_3$ hydrolyzable alkoxy group and the rest of $A_1$, $A_2$, $A_3$ is/are alkyl group(s).

2. The polymer compound for biomedical use according to claim 1, wherein the ethylenically unsaturated polymerizable monomer (a) having an alkylene glycol residue is a monomer represented by the following general formula [1],

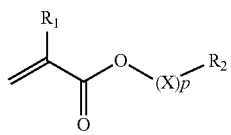

Formula [1]

wherein $R_1$ is a hydrogen atom or a methyl group, $R_2$ is a hydrogen atom or an alkyl group having 1 to 20 carbon atoms; X is an alkylene glycol residue having 1 to 10 carbon atoms; p is an integer from 1 to 100; in a case that p is an integer no less than 2, the repeated X may be the same or may be different.

3. The polymer compound for biomedical use according to claim 1, wherein the ethylenically unsaturated polymerizable monomer (a) having an alkylene glycol residue is methoxypolyethylene glycol acrylate or methoxypolyethylene glycol methacrylate.

4. The polymer compound for biomedical use according to claim 3, wherein an average repeating number of the alkylene glycol residue of the methoxypolyethylene glycol acrylate and/or methoxypolyethylene glycol methacrylate is 3 to 100.

5. The polymer compound for biomedical use according to claim 1, wherein the functional group of the ethylenically unsaturated polymerizable monomer (b) having a functional group for fixing a biologically active substance is at least one functional group selected from an aldehyde group, an active ester, an epoxy group, a vinyl sulfone group and biotin.

6. The polymer compound for biomedical use according to claim 1, wherein the ethylenically unsaturated polymerizable monomer (b) having a functional group for fixing a biologically active substance is a monomer having an active ester and represented by the following general formula [2],

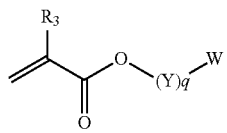

Formula [2]

wherein $R_3$ is a hydrogen atom or a methyl group, Y is an alkyl group or an alkylene glycol residue having 1 to 10 carbon atoms; W is an active ester group; q is an integer from 1 to 20; in a case that q is an integer no less than 2 and no more than 20, the repeated Y may be the same or may be different.

7. The polymer compound for biomedical use according to claim 5 or 6, wherein the active ester is selected from the group consisting of p-nitrophenyl ester and N-hydroxysuccinimide ester.

8. A surface coating material for biomedical use comprising a polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group, wherein the ethylenically unsaturated polymerizable monomer (c) having a cross-linkable functional group is a monomer having an alkoxysilyl represented by the following general formula [3],

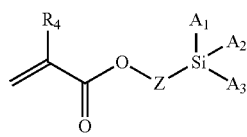

Formula [3]

wherein $R_4$ is a hydrogen atom or a methyl group, Z is an alkyl group having 1 to 20 carbon atoms; at least one of $A_1$, $A_2$, $A_3$ is hydrolyzable alkoxy group and the rest of $A_1$, $A_2$, $A_3$ is/are alkyl group(s).

9. A biochip substrate obtained by forming a layer comprising a polymer compound for biomedical use on a surface of a supporting substrate, the polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group, wherein the ethylenically unsaturated polymerizable monomer (c) having a cross-linkable functional group is a monomer having an alkoxysilyl represented by the following general formula [3],

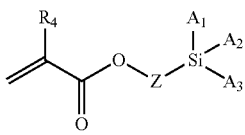

Formula [3]

wherein $R_4$, is a hydrogen atom or a methyl group, Z is an alkyl group having 1 to 20 carbon atoms; at least one $A_1$, $A_2$, $A_3$ is hydrolyzable alkoxy group and the rest of $A_1$, $A_2$, $A_3$ is/are alkyl group(s), and wherein the supporting substrate is made of a saturated cyclic polyolefin.

10. A method of manufacturing a biochip substrate, the method comprising the processes of:

applying a solution containing a polymer compound for biomedical use onto a surface of a supporting substrate to form a layer, the polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group, wherein the ethylenically unsaturated polymerizable monomer (c) having a cross-linkable functional group is a monomer having an alkoxysilyl represented by the following general formula [3],

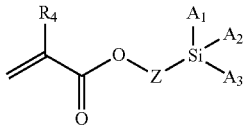

Formula [3]

wherein $R_4$ is a hydrogen atom or a methyl group, Z is an alkyl group having 1 to 20 carbon atoms; at least one of $A_1$, $A_2$, $A_3$ is hydrolyzable alkoxy group and the rest of $A_1$, $A_2$, $A_3$ is/are alkyl group(s); and after the applying process, cross-linking the polymer compound.

11. A biochip obtained by fixing a biologically active substance on a layer comprising a polymer compound for biomedical use of a biochip substrate obtained by forming a layer comprising a polymer compound for biomedical use on a surface of a supporting substrate, the polymer compound for biomedical use obtained by copolymerizing an ethylenically unsaturated polymerizable monomer (a) having an alkylene glycol residue, an ethylenically unsaturated polymerizable monomer (b) having a functional group for fixing a biologically active substance and an ethylenically unsaturated polymerizable monomer (c) having a cross-linkable functional group, wherein the ethylenically unsaturated polymerizable monomer (c) having a cross-linkable functional group is a monomer having an alkoxysilyl represented by the following general formula [3],

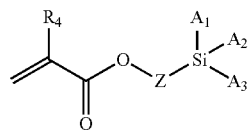

Formula [3]

wherein $R_4$ is a hydrogen atom or a methyl group, Z is an alkyl group having 1 to 20 carbon atoms; at least one of $A_1$, $A_2$, $A_3$ is hydrolyzable alkoxy group and the rest of $A_1$, $A_2$, $A_3$ is/are alkyl group(s).

12. A biochip according to claim 11, wherein the biologically active substance is at least one substance selected from nucleic acid, aptamer, protein, oligopeptide, sugar chain and glycoprotein.

* * * * *